United States Patent [19]

Markfelt

[11] 4,050,315

[45] Sept. 27, 1977

[54] REMOTELY ACTUATED SAMPLING APPARATUS

[75] Inventor: Reinhold S. Markfelt, Minneapolis, Minn.

[73] Assignee: UOP Inc., Des Plaines, Ill.

[21] Appl. No.: 748,257

[22] Filed: Dec. 6, 1976

[51] Int. Cl.² ............................................. G01N 1/12
[52] U.S. Cl. .............................................. 73/425.4 R
[58] Field of Search ................................... 73/425.4 R

[56] References Cited

U.S. PATENT DOCUMENTS

| 1,210,487 | 1/1917 | Kaul ..................................... 73/425.4 |
| 1,947,592 | 2/1934 | Haller ............................. 33/126.4 R |
| 2,198,116 | 4/1940 | Jurs .................................. 73/425.4 R |
| 4,004,463 | 1/1977 | Puthoff ........................... 73/425.4 R |

FOREIGN PATENT DOCUMENTS 607,352   10/1960   Canada .................................... 73/155

*Primary Examiner*—S. Clement Swisher

*Attorney, Agent, or Firm*—James R. Hoatson, Jr.; Barry L. Clark; William H. Page, II

[57] ABSTRACT

Apparatus for taking liquid samples in a well at any desired level under the surface includes a bullet-nosed tubular body with a weighted lower end and an elongated sampling chamber. The chamber has a circular inlet opening at its upper end which is sealed at its upper surface by a ball-shaped valve member to keep liquid out of the chamber as the body is lowered in the well. The valve member is attached at its upper end to a rod member guided in the body and suspended by a cable. A sharp jerk on the cable when the body is at the desired depth releases a detent holding means between the rod and body and lifts the valve member off its seat so that liquid can enter the chamber. A floating ball in the chamber engages the bottom of the circular opening when the chamber is filled with liquid to seal in the sample and prevent its contamination by liquid at higher levels as the body is raised to the surface.

7 Claims, 4 Drawing Figures

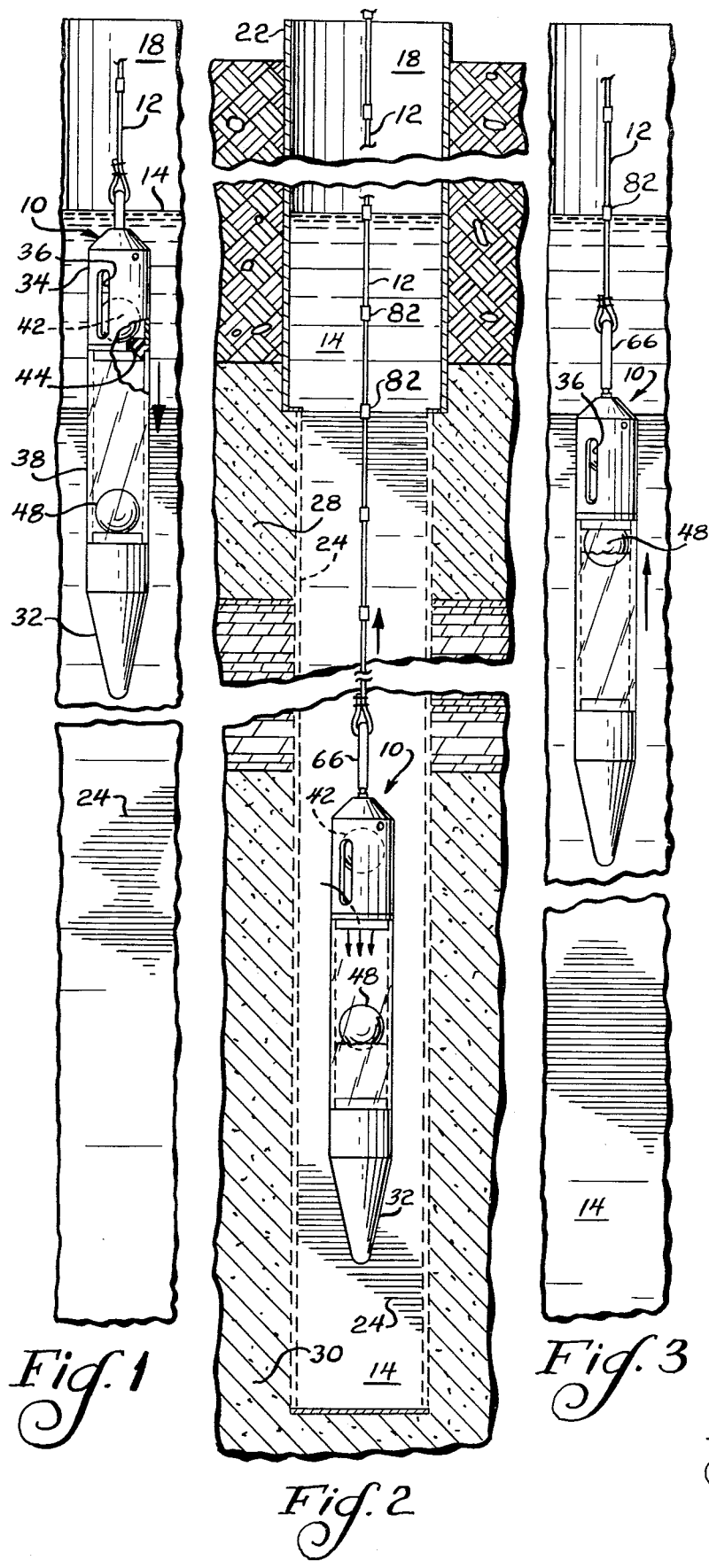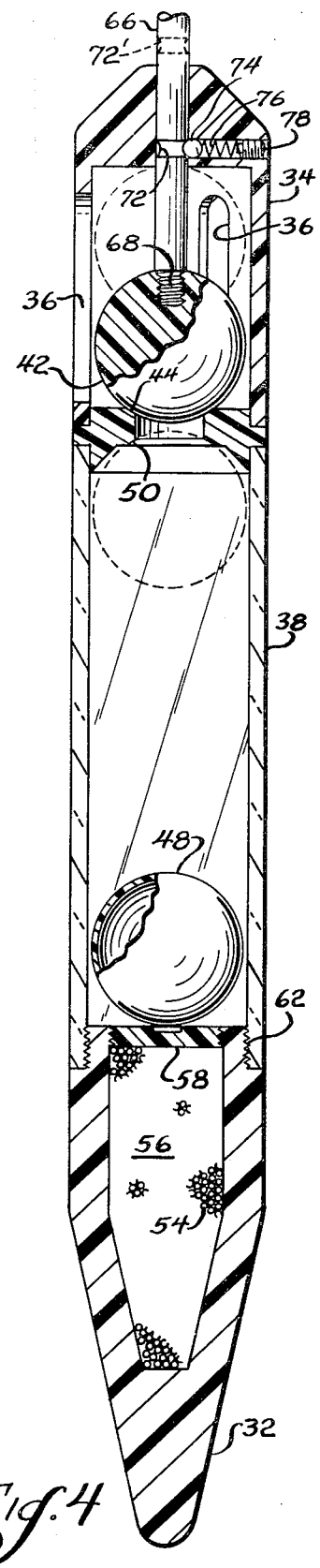

REMOTELY ACTUATED SAMPLING APPARATUS

BACKGROUND OF THE INVENTION

The invention relates to sampling devices for sampling liquid at a selected level below the liquid surface in a well. Where liquids such as water or oil seep into a well from different vertically spaced strata, the liquids usually tend to remain separated, at least in an observation well or in a normally pumped well when the liquid is not being pumped out. Since liquid from one strata might be more desirable than from another, it is necessary to be able to determine the depth at which favorable flow conditions exist. Once found, one may achieve a well providing only desirable liquid by using solid casing in the strata of undesirable liquid and a well screen in the strata of desirable liquid. One type of apparatus for water sampling in a remote location is disclosed in Mogg et al. U.S. Pat. No. 3,930,754. In the latter apparatus a portable cylinder of gas is used and the gas is injected down one tube to a desired level where it displaces water and pumps it to the surface. Although the patented apparatus performs well, it would be desirable to have an even more lightweight, economical and easy to carry device.

SUMMARY

It is among the objects of the present invention to provide a liquid sampler which can sample liquid at any desired location below the surface in a well and which is easy to operate, easy to carry, and economical to produce.

These and other objects are achieved by the sampling apparatus of the present invention which is briefly described in the Abstract.

The principal use of the invention is in observation wells which are usually small diameter wells drilled in the vicinity of larger producing wells and often located in remote places accessible only on foot. Where the observation wells are provided with a perforated casing or well screens in contact with different water bearing strata, they will, due to their small diameter and lack or turbulence inducing means in the water, tend to maintain the column of water in distinctly separated layers in the regions adjacent to strata having water with different properties. Thus, if a series of samples of water can be drawn from different levels, one might determine there is a particularly desirable collection level in either the well being sampled or other wells already located, or to be located, close to the sample well. For existing wells having water inflow at two or more spaced locations, the sampler could also be used to select the most desirable location for the pump.

BRIEF DESCRIPTION OF THE DRAWINGS

FIG. 1 is a fragmentary cross-section through a well casing showing the improved sampler being lowered into a well;

FIG. 2 is a view similar to FIG. 1 showing a liquid sample flowing into the improved sampler just after its upper sealing valve is released;

FIG. 3 is a view similar to FIG. 1 showing the improved sampler being withdrawn from the well; and FIG. 4 is a cross-section of a sampler made in accordance with my invention.

DESCRIPTION OF THE PREFERRED EMBODIMENT

Referring to FIG. 1, my improved sampling device is indicated generally at 10 and is shown as being lowered by a cable 12 into a column of water 14 in a well 18. As can be seen in FIG. 2, the well 18 has a casing comprising an upper smooth pipe section 22 and a lower perforated pipe or well screen portion 24. As shown, water may enter the well from either the upper water-bearing formation 28 or the lower water-bearing formation 30. For purposes of illustration, it will be assumed that the person lowering the device 10 into the well desires to lower the device through the water from the upper formation 28 without sampling any of it and to take a sample of the water from the lower formation 30.

As seen in FIG. 4, the sampling device includes a lower bullet-nosed housing end portion 32 which may be made of a suitable plastic such as ABS or nylon and an upper housing portion 34 which contains a plurality of elongated slots 36 through which water may enter a central hollow tubular chamber 38 when a spherically-shaped upper valve member 42 is lifted off an upper valve seat 44 into the dotted line position shown. As water rushes into the sampling chamber, as indicated by the arrows in FIG. 2, a lower floating valve member 48 which has a density less than that of the liquid in the well and which may comprise a hollow plastic ball, is carried upwardly by the increasing water level in the chamber until it seals against the lower valve seat 50 as shown in dotted lines in FIG. 4. Once the chamber 38 is filled, the device may be lifted by means of cable 12 as indicated by the arrow in FIG. 3. Since the floating valve member 48 will be sealed, there is no danger of contamination of the sample as the apparatus passes upwardly through the portion of the well which has received water from upper formation 28.

To increase its density, which, of course, must be greater than the density of the liquid in the well, the apparatus is preferably weighted such as by use of lead shot 54 in a chamber 56 covered by a cap member 58. Where access to the interior of chamber 38 for cleaning purposes appears desirable, the tubular chamber 38 may be attached to the housing end portion 32 by screw thread means 62. The tubular portion 38 is preferably made of a suitable transparent plastic but could also be made of non-transparent materials. The actuation of the upper valve member 42 when the sampling device is at the proper depth is controlled by valve actuating rod member 66. The rod 66 is preferably adjustably threadably engaged with the solid plastic valve member 42 so that sealing contact between the valve member 42 and the valve seat 44 can be achieved when a detent groove 72 in the rod 66 is engaged by a detent ball member 74. The ball 74 is mounted in an aperture in the upper housing portion 32 and is forced into the detent groove 72 by a spring 76 and a set screw 78. Although only one detent ball 74 is shown in FIG. 4, it is preferable to have an identical ball on the opposite side of the detent groove 72 in order to balance the forces on the rod 66.

In operation, when the sampling device is at the proper depth as indicated by depth markings 82 on the cable 12, the operator gives a sharp jerk to the cable 12 which causes the detent groove 72 in rod 66 to become disengaged from the balls 74 and to move to the dotted line position 72' so that water entering the slots 36 can pass into the chamber 38. The depth markings 82 may comprise pieces of pressure-sensitive tape which are squeezed against each other or may be short lengths of tubing which are slid along the cable 12 and then heat shrunk into engagement with the cable after they have been properly spaced. The cable 12 may be made of any suitable material but is preferably made of a material that will not stretch, such as a twisted steel cable.

I claim as my invention:

1. A sampling device for taking a sample of liquid at any desired level in a well and sealing the sample against possible contamination by liquid at a higher level as the device is withdrawn; said device having an average density greater than the liquid and including an integral sample receiving chamber portion intermediate its ends which is closed at the lower end of said chamber portion and has an opening at the top of said chamber portion which may be selectively closed; said opening being formed in a ring-like portion which includes upper and lower valve seat portions; a ball having a density lower than said liquid positioned in said chamber and adapted to be lifted by liquid entering said opening until said ball rests on said lower valve seat portion; an upper valve member mounted on an upwardly extending rod member for movement into or out of engagement with said upper valve seat portion; said rod member having first detent means thereon engageable with second detent means in an upper housing portion of said device to normally selectively lock said rod with said upper valve member in its position of engagement with said upper valve seat portion; and cable means extending upwardly from said rod for lowering or raising said device, said cable means being sufficiently strong as to resist breakage when a snapping force is applied thereto to cause said first and second detent means to become disengaged.

2. The sampling device of claim 1 wherein said device includes a pointed housing lower end portion extending downwardly from said receiving chamber portion, said pointed housing portion being removably attached to said receiving chamber and forming the lower end thereof.

3. The sampling device of claim 2 wherein said pointed housing portion contains weights which increase the density of said device.

4. The sampling device of claim 1 wherein said upper valve member comprises a solid ball and said ball which is positioned in said chamber is hollow.

5. The sampling device of claim 1 wherein said upper valve member is adjustably mounted on said rod member so as to vary the contact pressure on said upper valve seat portion when said rod member is locked by said detent means.

6. The sampling device of claim 1 wherein said first detent means comprises a groove and said second detent means includes at least one spring loaded ball movable radially in said upper housing portion into normally engaged relation with said groove.

7. The sampling device of claim 1 wherein said cable means includes spaced indicia thereon for showing the depth to which said device has been lowered.

* * * * *